(12) United States Patent
Devisetty et al.

(10) Patent No.: US 10,375,950 B2
(45) Date of Patent: Aug. 13, 2019

(54) CONCENTRATED GIBBERELLIN SOLUTION FORMULATIONS

(71) Applicant: Valent BioSciences Corporation, Libertyville, IL (US)

(72) Inventors: Bala N. Devisetty, Buffalo Grove, IL (US); Gregory D. Venburg, Deerfield, IL (US)

(73) Assignee: VALENT BIOSCIENCES LLC, Libertyville, IL (US)

( * ) Notice: Subject to any disclaimer, the term of this patent is extended or adjusted under 35 U.S.C. 154(b) by 0 days.

(21) Appl. No.: 15/371,409

(22) Filed: Dec. 7, 2016

(65) Prior Publication Data

US 2017/0156323 A1   Jun. 8, 2017

Related U.S. Application Data

(60) Provisional application No. 62/263,830, filed on Dec. 7, 2015.

(51) Int. Cl.
  *A01N 43/12*   (2006.01)
  *A01N 25/30*   (2006.01)
  *A01N 25/02*   (2006.01)

(52) U.S. Cl.
  CPC .................. *A01N 25/02* (2013.01)

(58) Field of Classification Search
  CPC ......... A01N 25/02; A01N 43/12; A01N 45/00
  See application file for complete search history.

(56) References Cited

U.S. PATENT DOCUMENTS

| | | |
|---|---|---|
| 4,936,901 A | 6/1990 | Surgant, Sr. et al. |
| 5,622,658 A | 4/1997 | Lloyd et al. |
| 6,984,609 B2 | 1/2006 | Devisetty et al. |
| 2003/0008949 A1 | 1/2003 | Devisetty et al. |
| 2006/0166898 A1* | 7/2006 | Chen ............... A01N 25/04 514/22 |
| 2012/0180701 A1* | 7/2012 | Benson ............ C04B 14/365 106/471 |
| 2013/0225410 A1 | 8/2013 | Haas |
| 2013/0225411 A1* | 8/2013 | Buchholz ............ A01N 43/90 504/313 |
| 2015/0080216 A1* | 3/2015 | Wikeley ............. A01N 43/08 504/136 |
| 2015/0173365 A1* | 6/2015 | Devisetty ........... A01N 43/12 504/297 |
| 2017/0013836 A1† | 1/2017 | Sheth |

FOREIGN PATENT DOCUMENTS

EP   0 252 897   1/1988

OTHER PUBLICATIONS

Biobased Propylene Glycol, Orison Marketing, 2012.*
International Search Report and Written Opinion issued by the International Bureau in corresponding application No. PCT/US2016/065267 dated Feb. 17, 2017.

\* cited by examiner
† cited by third party

*Primary Examiner* — Johann R Richter
*Assistant Examiner* — Genevieve S Alley
(74) *Attorney, Agent, or Firm* — Wood, Phillips, Katz, Clark & Mortimer

(57) ABSTRACT

The present invention relates to concentrated gibberellin formulations and methods of their use.

18 Claims, No Drawings

CONCENTRATED GIBBERELLIN SOLUTION FORMULATIONS

FIELD OF THE INVENTION

The present invention relates to concentrated gibberellin solution formulations.

BACKGROUND OF THE INVENTION

Gibberellins are a class of plant growth regulators which are diterpenoid acids. Gibberellins are commercially produced by fermentation of a natural fungus, *Gibberella fugikuroi*. Gibberellins are marketed under various trade names and are commercially used on a variety of fruit orchards, vegetable crops, row crops, and ornamental crops. The predominantly used gibberellin is gibberellin acid ("$GA_3$").

Gibberellins have been formulated in numerous ways over the years in order to attempt to overcome their low solubility. For example, gibberellins have been formulated for foliar application as solutions, soluble powders, wettable powders, tablets, and water-dispersible granules, and soluble granules. The disadvantages of each category of the prior art formulations are discussed below.

Solution formulations of the prior art are disadvantageous in several respects. The formulations are less concentrated due to low solubility of gibberellins, have limited storage stability, and/or contain unacceptable amounts of volatile organic compounds ("VOCs").

The low solubility of $GA_3$, gibberellin$_4$ ("$GA_4$"), gibberellin$_7$ ("$GA_7$"), or gibberellin$_{4/7}$ ("$GA_{4/7}$") in some solvents, such as propylene glycol, does not permit preparation of high concentration solution formulations. These low strength solution formulations require larger packaging, more storage space, and higher associated transportation, warehousing, and container disposal costs. Due to very low solubility and undesirable hydrolysis, it has been especially difficult to formulate $GA_3$ in aqueous systems.

In order to overcome solubility issues, some formulations use solvents with amounts of VOCs that are not safe for the environment. For example, isopropyl alcohol and methyl alcohol offer severe disadvantages such as flammability and toxicity, which lead to restrictions in manufacturing, packaging, labeling, transportation, and warehousing of such solutions. Tetrahydrofurfuryl alcohol ("THFA") is considered corrosive to the eye and skin.

One way to overcome the solubility issues with $GA_3$, $GA_4$, and $GA_{4/7}$ is to prepare soluble powder formulations. These powder formulations dissolve readily when mixed with water and form true solutions. Once the solution is formed, no further mixing or agitation of the tank-mix is required.

Another way to overcome the solubility issues is to create a wettable powder. A wettable powder formulation is a dry, finely ground formulation. In this type of formulation, the active ingredient is combined with a finely ground dry carrier, usually a mineral clay, along with other ingredients that enhance the ability of the powder to be suspended in water. Upon mixing the wettable powder with water, a suspension is formed, which is then applied by a spray technique. Often the spray liquid must be continuously mixed to prevent settling of insoluble compositions.

However, wettable powders and soluble powder formulations tend to produce dust upon handling, such as when pouring, transferring or measuring them. This dust may pose health hazards. Further, powder formulations tend to wet poorly and also solubilize slowly upon addition to water. Powder formulations thus take longer to wet, disperse and solubilize in a tank-mix. Formation of lumps or partially solubilized spray solutions will lead to uneven distribution of the plant growth regulator in the tank-mix with the potential for reduced field performance. Sometimes, foam in the spray tank caused by spray tank adjuvants can also affect wetting and solubility of wettable and soluble powders. Wettable powder formulations will also leave undesirable insoluble residues both in the tank and on the sprayed foliage and fruit.

Another type of agricultural formulation is a tablet. Tablet formulations are pre-measured dosage delivery systems. They are useful in small areas, or for ornamental purposes. Tablet formulations may be effervescent, which dissolve in water over a period of two to ten minutes depending upon the type and size of the tablet. However, tablets generally deliver only between 0.1 to 1 gram of active ingredient per tablet. They are not ideal for large-scale field operations. Moreover, effervescent tablets are highly susceptible to humidity and may be slow to dissolve and are expensive.

Yet another type of agricultural formulation is a water-dispersible granule. Water-dispersible granules are also known as wettable granules or dry flowables. This type of formulation is similar to a wettable powder, except that the active ingredient is formulated as a dispersible granule. To prepare the water-dispersible granules for spray application, they are dispersed in water and form a suspension upon agitation. Many different water-dispersible granular formulations are known for agricultural chemicals. For example, EP 0 252 897 and U.S. Pat. No. 4,936,901 disclose encapsulated plant growth regulators in water dispersible granular formulations; and U.S. Pat. No. 5,622,658 discloses an extrudable composition for preparing water-dispersible granules.

Water-dispersible granules usually have no greater than eight percent moisture content, and form suspensions when added to aqueous solutions. The resulting suspension must be agitated for a period of time in order to fully disperse it. Agitation or by-pass recirculation of the tank-mix must also be maintained during application. The quality of water-dispersible granules is highly process- and active-ingredient-dependent; and can result in low yield recoveries, poor attrition resistance leading to dust potential, high manufacturing cost and poor dispersion. Generally, sprays of dissolved water-dispersible granular formulations leave undesirable insoluble residues on the treated foliage and fruit.

For $GA_3$, $GA_4$, $GA_7$, and $GA_{4/7}$ formulations to be efficacious, the active ingredient must solubilize in tank-mixes prior to application. Otherwise, product efficacy will be severely affected. When water-dispersible granules are used, the grower often may not realize if he has achieved complete solubility of the active ingredient in the spray solutions. In addition, water-dispersible granules can harden over time and thus result in poor dispersibility and solubility of the active ingredient. Dust and caking may be problems with certain water-dispersible granules and powder formulations.

U.S. Pat. No. 6,984,609 B2 discloses a concentrated, water soluble granular plant growth regulatory formulation that is commercially available as ProGibb 40% (available from Valent BioSciences Corporation). The disclosed granules swiftly dissolve in water and provide a true solution at the use rates without any insoluble particulates in the spray mixture. However, some orchard and vegetable growers would prefer solution formulations that are safer to handle and easier to apply. The formulation being highly concentrated is not suitable for direct application to the soil or to rice growing aqueous environments.

Despite all of these formulation options, currently there are not any commercial gibberellin formulations which are suitable for application to the soil. Soil application is desirable because it places the gibberellin in close proximity to the root system which can absorb the gibberellin.

Therefore, there is a need for environmentally safe, non-phytotoxic, efficacious, high strength gibberellin solution formulations. The improved formulations should overcome the toxicity, handling, storage, transportation, and solubility issues encountered by prior art formulations. The high strength solution formulations should allow development of granular formulations for direct application to soil. As granules specifically sand based do not have absorption capacity high strength gibberellic acid solutions should allow coating the granular surface uniformly. Granular formulations are ideal for direct application to the soil and plant growing environment such as wetland rice. In addition, high strength solutions are also ideal for reducing costs associated with solvent, storage, and transportation.

SUMMARY OF THE INVENTION

In one aspect, the present invention is directed to concentrated agricultural solution formulations comprising from about 5 to about 15% wt/wt of at least one gibberellin selected from the group consisting of $GA_3$, $GA_4$, $GA_7$ and $GA_{4/7}$, from about 75 to about 90% wt/wt of at least one solvent selected from the group consisting of polyethylene glycols with average molecular weights of from about 190 to about 420 daltons and C8 to C12 fatty acid dimethylamides, from about 0.1 to about 4% wt/wt of a binder, and from about 0.1 to about 3% wt/wt of a non-ionic surfactant.

In a further embodiment, the formulations comprise from about 5 to about 15% wt/wt of at least one gibberellin selected from the group consisting of $GA_3$, $GA_4$, $GA_7$ and $GA_{4/7}$, from about 75 to about 90% wt/wt polyethylene glycols with average molecular weights of from about 190 to about 210 daltons, from about 0.1 to about 4% wt/wt of a binder selected from the group consisting of alkylated vinyl pyrrolidone polymers, a copolymer of acetic acid ethenyl ester and 1-ethenyl-2-pyrrolidinone, and a copolymer of polyvinylpyrrolidone and 1-eicodecene, and from about 0.1 to about 3% wt/wt of a non-ionic surfactant selected from the group consisting of polyoxyethylene (20) sorbitan monolaurate and polyoxyethylene (20) sorbitan monooleate.

In another aspect, the invention is directed to methods for regulating plant growth comprising treating soil or a plant with an effective amount of the formulations of the present invention.

DETAILED DESCRIPTION OF THE INVENTION

Despite gibberellins' known stability issues, Applicant has unexpectedly discovered that formulations with from about 75 to about 90% wt/wt of at least one solvent selected from the group consisting of polyethylene glycols with average molecular weights of from about 190 to about 420 daltons and C8 to C12 fatty acid dimethylamides, from about 0.1 to about 4% wt/wt of a binder, and from about 0.1 to about 3% wt/wt of a non-ionic surfactant allowed for stable, concentrated gibberellin formulations. These concentrated gibberellin formulations are versatile as they can be diluted with water and/or used as pre-mix concentrates to provide formulations for soil application.

In one embodiment, the present invention is directed to concentrated agricultural solution formulations comprising from about 5 to about 15% wt/wt of at least one gibberellin selected from the group consisting of $GA_3$, $GA_4$, $GA_7$ and $GA_{4/7}$, from about 75 to about 90% wt/wt of at least one solvent selected from the group consisting of polyethylene glycols with average molecular weights of from about 190 to about 420 daltons and C8 to C12 fatty acid dimethylamides, from about 0.1 to about 4% wt/wt of a binder, and from about 0.1 to about 3% wt/wt of a non-ionic surfactant.

In a preferred embodiment, the gibberellin is $GA_3$.

In another embodiment, the formulation comprises from about 9 to about 12% wt/wt of at least one gibberellin. In a preferred embodiment, the formulations comprise from about 9.5 to about 11.5% wt/wt of at least one gibberellin. In a most preferred embodiment, the formulations comprise about 10.6% wt/wt at least one gibberellin.

In a further embodiment, the formulations comprise from about 0.1 to about 4% wt/wt of a color additive. In a preferred embodiment, the color additive is a dye. In a more preferred embodiment, the dye is a FD&C food grade dye. In an even more preferred embodiment, the dye is selected from the group consisting of FD&C Blue #1, FD&C Blue #2, FD&C Green #3, FD&C Red #3, FD&C Red #40, FD&C Yellow #5, FD&C Yellow #6, and Citrus Red #2. In a most preferred embodiment, the dye is FD&C Blue #1. In another most preferred embodiment, the dye is FD&C Red #40.

As used herein, "FD&C" refers to the United States' Food, Drug, and Cosmetic Act which is United States Code, Title 21. This code provides the following list (as of October 2015) of food grade color additives which may be added to foods: FD&C Blue #1; FD&C Blue #2; FD&C Green #3; FD&C Red #3; FD&C Red #40; FD&C Yellow #5; FD&C Yellow #6; and Citrus Red #2.

Polyethylene glycol ("PEG") is a polyether compound with the structure: $H-(O-CH_2-CH_2)_n-OH$. PEGs are prepared by polymerization of ethylene oxide and are commercially available over a wide range of molecular weights. The number following "polyethylene glycol," or "PEG," refers to the molecular weight. For example, PEG 200 has a range of molecular weights from 190 to 210, PEG 300 from 285 to 315, and PEG 400 from 380 to 420 daltons. In a preferred embodiment, the solvent is polyethylene glycols with average molecular weights of from about 190 to about 420 daltons. In a more preferred embodiment, the solvent is polyethylene glycols with average molecular weights of from about 190 to about 210 daltons.

In another embodiment, the solvent is at least one C8 to C12 fatty acid dimethylamide. In a preferred embodiment, the solvent is a mixture of C8 to C10 fatty acid dimethylamides or a mixture of C10 to C12 fatty acid dimethylamides. In a more preferred embodiment, the solvent is a mixture of C8 to C10 fatty acid dimethylamides. A mixture of C8 to C10 fatty acid dimethylamides is commercially available as Agnique® AMD 810 (Agnique is available from BASF and a registered trademark of Cognis Corporation).

In a further embodiment, the solvent is a mixture of: (1) polyethylene glycols with average molecular weights of from about 190 to about 210 daltons; and (2) a mixture of C8 to C10 fatty acid dimethylamides.

In an embodiment, the binder is selected from the group consisting of alkylated vinyl pyrrolidone polymers, a copolymer of acetic acid ethenyl ester and 1-ethenyl-2-pyrrolidinone, and a copolymer of polyvinylpyrrolidone and 1-eicodecene. In a preferred embodiment, the binder is a copolymer of acetic acid ethenyl ester and 1-ethenyl-2-pyrrolidinone (available from Ashland as Agrimer™ VA-6). Alklated vinyl pyrrolidone polymers, such as Agrimer™ AL10, and a copolymer of polyvinylpyrrolidone and 1-eicodecene, Agrimer™ VA-71, are also available from Ashland.

In a further embodiment, the formulations comprise from about 1 to about 3% wt/wt of the binder. In a preferred embodiment, the formulations comprise from about 1.5 to about 2.5% wt/wt of the binder. In a more preferred embodiment, the formulations comprise about 2% wt/wt of the binder.

In another embodiment, the non-ionic surfactant is selected from the group consisting of polyoxyethylene (20) sorbitan monolaurate and polyoxyethylene (20) sorbitan monooleate. In a preferred embodiment, the non-ionic surfactant is polyoxyethylene (20) sorbitan monolaurate.

In an embodiment, the formulations comprise from about 0.1 to about 2% wt/wt of the non-ionic surfactant. In a preferred embodiment, the formulations comprise from about 0.5 to about 1.5% wt/wt of the non-ionic surfactant. In a more preferred embodiment, the formulations comprise about 1% wt/wt of the non-ionic surfactant.

In a further embodiment, the formulations comprise from about 5 to about 15% wt/wt of at least one gibberellin selected from the group consisting of gibberellic acid ($GA_3$), gibberellin$_4$ ($GA_4$), gibberellin$_7$ ($GA_7$) and gibberellin$_{4/7}$ ($GA_{4/7}$), from about 75 to about 90% wt/wt polyethylene glycols with average molecular weights of from about 190 to about 210 daltons, from about 0.1 to about 4% wt/wt of a binder selected from the group consisting of alkylated vinyl pyrrolidone polymers, a copolymer of acetic acid ethenyl ester and 1-ethenyl-2-pyrrolidinone, and a copolymer of polyvinylpyrrolidone and 1-eicodecene, and from about 0.1 to about 3% wt/wt of a non-ionic surfactant selected from the group consisting of polyoxyethylene (20) sorbitan monolaurate and polyoxyethylene (20) sorbitan monooleate. In a preferred embodiment, the gibberellin is $GA_3$. In another preferred embodiment, the binder is a copolymer of acetic acid ethenyl ester and 1-ethenyl-2-pyrrolidinone. In yet another preferred embodiment, the non-ionic surfactant is polyoxyethylene (20) sorbitan monolaurate.

In yet another embodiment, the present invention is directed to methods for regulating plant growth comprising treating a plant or soil with an effective amount of a formulation of the present invention.

The formulations of the present invention are also low VOC formulations. This means that the formulations contain less than or equal to 25% emission potential, as determined by thermo gravimetric analysis ("TGA"). Gibberellin formulations with greater than 25% emission potential, as determined by TGA, are considered High-VOC products by CADPR (California Department of Pesticide Regulation). TGA involves heating a sample of the formulation in an environmentally controlled chamber while the rate of sample mass loss is measured. CADPR states that the emission potential of the formulation is determined by taking the mean of three replicate TGA measurements of the formulations and then subtracting the percent water and the exempt compounds from the measurement. The TGA process is well known by those of skill in the art.

In a further embodiment, the formulations of the present invention are applied to plants or soil at a rate of from about 0.1 to about 50 grams of gibberellin per acre. In a preferred embodiment, the formulations are applied to the plants or soil at a rate of from about 1 to about 20 grams of gibberellin per acre. In a more preferred embodiment, the formulations are applied to the plants or soil at a rate of from about 1 to about 10 grams of gibberellin per acre.

Formulations of the present invention may be used as a pre-mix product. For example, the pre-mix product can be added to a tank mix prior to application to the plants. Alternatively, the formulations of the present invention can be used as a pre-mix to pre-formed granular product for direct application to soil or plant growing environment.

Formulations of the present invention may be used on any plant in need of gibberellin treatment (or on the soil adjacent to the plant in need of treatment), for example, on: artichokes to accelerate maturity and increase yield; blueberries to improve fruit set and fruit size; bananas to stimulate plant growth and reduce effects of stress, or post-harvest for maintaining fruit quality; carrots to maintain foliage growth during periods of stress; celery to increase plant height and yield; cherries to increase fruit size, firmness and quality or to delay maturity for a more orderly harvest; citrus to increase fruit set and yield, to delay rind aging, reduce physiological disorders, or delay maturity for a more orderly harvest; collard greens to facilitate harvest, increase yield, and improve quality; cotton to promote early season growth and increase seedling vigor; and cucumbers to stimulate fruit set during periods of cool weather; pasture land used for animal grazing; and corn. The formulations can be used post harvest on bananas and citrus, etc. Formulations of the present invention could also be used on grapes, melons, pecans, peppers, pineapples, rice, rhubarb, spinach, stone fruits, sugarcane, wheat, strawberries, watercress and other plants in need of treatment.

In an embodiment, the formulations of the present invention are applied to a plant selected from the group consisting of rice, cotton, corn, soybeans, sugarcane, wheat and beets. In a preferred embodiment, the formulations of the present invention are applied to rice.

The disclosed embodiments are simply exemplary embodiments of the inventive concepts disclosed herein and should not be considered as limiting, unless the claims expressly state otherwise.

The term "effective amount" means the amount of the formulation that will provide the desired effect on the plant that is being treated. The "effective amount" will vary depending on the formulation concentration, the type of plants(s) being treated, and the result desired, among other factors. Thus, it is not always possible to specify an exact "effective amount." However, an appropriate "effective amount" in any individual case may be determined by one of ordinary skill in the art. For example, effective amounts of formulations of the present invention may be from about 0.1 to about 50 grams of gibberellin per acre.

Other components of the formulation may be included in nominal amounts that do not affect the storage stability characteristics of the present formulations. Additional components include additional surface active agents, crystal growth inhibitors, stickers, spreaders, leaf penetrants, dispersants, systemic acquired resistance inducers, systemic acquired resistance inhibiters, anti-foaming agents, preservatives, pH regulators, cosolvents, humectants, UV protectants, biostimulants, root growth promotors, biopesticides, inoculants, vehicles, sequestrants or other components which facilitate production, storage stability, product handling and application.

It is also contemplated that the ready-to-mix composition materials of this invention may be used in combination with other active ingredients, such as herbicides, fungicides, insecticides, bactericides, nematicides, biochemical pesticides, biostimulants, biopesticides, plant produced pesticides (botanicals), safeners or plant nutrients.

As used herein, the term "herbicide" broadly refers to compounds or compositions that are used as herbicides, as well as herbicide safeners and algicides. Herbicides may include, but are not limited to, 1,2,4-triazinones, 1,3,5-triazines, alkanamides (acetamides), anilides, aryloxyalkanoic acids, aryloxyphenoxypropionates, benzamides, benzamides (L), benzenedicarboxylic acids, benzofurans, benzoic acids (auxins), benzonitriles, benzothiadiazinones, benzothiazolones, carbamates (DHP), carbamates, chloroacetamides, cyclohexanedione oximes, dinitroanilines, dinitrophenols, diphenyl ethers, diphenyl ethers (cbi), glycine derivatives, halogenated alkanoic acids, hydroxybenzonitriles, imidazolinones, isoxazoles, isoxazolidinones, N-phenylphthalimides, organoarsenics, oxadiazoles, oxazolidinediones, oxyacetamides, phenoxycarboxylic acids, phenyl carbamate herbicides, phenylpyrazole herbicides, phenylpyridazines, phosphinic acids, phosphorodithioates, phthalamates, pyrazole herbicides, pyridazines, pyridazinones (PDS), pyridazinones (PSII), pyridines, pyridinecarboxamides, pyridinecarboxylic acids, pyrimidindiones, pyrimidines, pyrimidinyl-oxybenzoics, pyrimidinyloxybenzoic analogs, quinolinecarboxylic acids, BI class and IV including thiocarbamate, semi-carbazones, sulfonylaminocarbonyl-triazolinones, sulfonylureas, tetrazolinones, thiadiazoles, thiocarbamates, triazoles, triazolinones, triazolopyrimidines, triketones, uracils, ureas, 2,3,6-TBA, 2,4,5-T, 2,4-D, 2,4-D-2-ethylhexyl, 2,4-DB, 2,4-D-dimethylammonium, 2,4-D-isopropyl, 2,4-D-isopropyl, 2,4-D-trolamine (2,4-D-triethanolamine), ACD 10614, ACD 10435, acetochlor, acifluorfen, acifluorfen-sodium, aclonifen, acrolein, AD 67, alachlor, alloxydim-sodium, ametryn, amicarbazone, amidosulfuron, amitrole, ammonium sulfamate, anilofos, asulam, atraton, atrazine, azafenidin, azimsulfuron, aziprotryne, barban, beflubutamid, benazolin, benazolin-ethyl, benfluralin, benfuresate, benoxacor, bensulfuron-methyl, bensulide, bentazone, benzobicyclon, benzofenap, benzoylprop, enzoylprop-ethyl, bifenox, bilanafos-sodium, bispyribac-sodium, borax, bromacil, bromobutide, bromofenoxim, bromoxynil, bromoxynil octanoate, bromoxynil-potassium, brompyrazon, butachlor, butafenacil, butenachlor, buthidazole, butralin, butroxydim, buturon, cafenstrole, calcium cyanamide, carbetamide, carfentrazone-ethyl, chlomethoxyfen, chloramben, chlorbromuron, chlorbufam, chlorfenac, chlorfenac-sodium, chlorfenprop, chlorfenprop-methyl, chlorfenprop, chlorfenprop-ethyl, chlorflurenol-methyl, chloridazon, chlorimuron-ethyl, chlornitrofen, chloroacetic acid, chloro-toluron, chloroxuron, chlorpropham, chlorsulfuron, chlorthal-dimethyl, chlorthiamid, cinidon-ethyl, cinosulfuron, clethodim, sethoxydim, tepraloxydim, tralkoxydim, clodinafop-propargyl, clofop, clofop-isobutyl, clomazone, clomeprop, clopyralid, cloquintocet-mexyl, cloransulam-methyl, credazine, cumyluron, cyanamide, cyanazine, cyclosulfamuron, cycloxydim, cycluron, cyhalofop-butyl, cyometrinil, daimuron, dazomet, desmedipham, desmetryn, di-allate, dicamba, dichlobenil, dichlormid, dichlorprop, dichlorprop-isoctyl, dichlorprop-P, diclofop, diclofop-methyl, diclosulam, diethatyl-ethyl; diethatyl, difenoxuron, difenzoquat metilsulfate, diflufenican, diflufenzopyr, dikegulac, dikegulac-sodium, dimefuron, dimepiperate, dimethachlor, dimethametryn, dimethipin, dimethylarsinic acid, dinitramine dinoseb, dinoseb acetate, dinoterb, diphenamid, dipropetryn, disul, disul-sodium, dithiopyr, diuron, DNOC, DSMA, eglinazine-ethyl, eglinazine, EL 177, endothal, ethalfluralin, ethametsulfuron-methyl, ethidimuron, ethofumesate, ethoxysulfuron, etobenzanid, fenchlorazole-ethyl, fenclorim, fenoprop, fenoprop-butotyl, fenoxaprop-ethyl, fenoxaprop, fenoxaprop-P, fenoxaprop-P-ethyl, fenthiaprop, fenthiaprop-ethyl, fentrazamide, fenuron, flamprop-methyl, flamprop-isopropyl, flamprop, flamprop-M-isopropyl, flamprop-M-methyl, flazasulfuron, florasulam, fluazifop-butyl, fluazifop-P, fluazifop-P-butyl, fluazolate, flucarbazone-sodium, fluchloralin, flufenacet, flumetsulam, flumiclorac-pentyl, flumioxazin, flumipropyn, fluometuron, fluorodifen, fluoroglycofen-ethyl, fluothiuron, flupoxam, flupropanate-sodium, flupyrsulfuron-methyl-sodium, flurazole, flurenol-butyl, fluridone, flurochloridone, fluroxypyr, fluroxypyr-meptyl, flurtamone, fluthiacet-methyl, fomesafen, foramsulfuron, fosamine-ammonium, furilazole, glufosinate-ammonium, glyphosate, glyphosate-ammonium, glyphosate-isopropylammonium, glyphosate-sodium, glyphosate-trimesium, halosulfuron-methyl, haloxyfop, haloxyfop-etotyl, haloxyfop-P, hexaflurate, hexazinone, imazamethabenzmethyl, imazamox, imazapic, imazapyr, imazapyr-isopropylammonium, imazaquin, imazethapyr, imazosulfuron, indanofan, iodosulfuron-methyl-sodium, ioxynil, ioxynil octanoate, ioxynil-sodium, isocarbamid, isocil, isomethiozin, isonoruron, isoproturon, isouron, isoxaben, isoxaflutole, isoxapyrifop, karbutilate, lactofen, lenacil, linuron, LS830556, maleic hydrazide, MCPA, MCPA-thioethyl, MCPB, MCPB-ethyl, mecoprop, mecoprop-P, medinoterb acetate, medinoterb, mefenacet, mefenpyrdiethyl, mefluidide, mesosulfuron-methyl, mesotrione, metamifop, metamitron, metazachlor, methabenzthiazuron, methazole, methiuron, methoprotryne, methoxyphenone, methyl isothiocyanate, methylarsonic acid, methyldymron, metobenzuron, metobromuron, metolachlor, metosulam, metoxuron, metribuzin, metsulfuron-ethyl, MK-616, monalide, monolinuron, monuron, monuron-TCA, MSMA, naphthalic anhydride, naproanilide, napropamide, naptalam, NC-330, neburon, nicosulfuron, nitralin, nitrofen, norflurazon, orbencarb, oryzalin, oxabetrinil, oxadiargyl, oxadiazon, oxasulfuron, oxaziclomefone, oxyfluorfen, pendimethalin, penoxsulam, pentachlorophenol, pentanochlor, pentoxazone, perfluidone, pethoxamid, phenisopham, phenmedipham, phenylmercury acetate, picolinafen, primisulfuron-methyl, prodiamine, profluralin, proglinazine-ethyl, proglinazine, prometon, prometryn, propachlor, propanil, propaquizafop, propazine, propham, propisochlor, propoxycarbazone-sodium, propyzamide, prosulfuron, pyraflufen-ethyl, pyrazolynate, pyrazosulfuron-ethyl, pyrazoxyfen, pyribenzoxim, pyributicarb, pyridate, pyriftalid, pyriminobac-methyl, pyrithiobac-sodium, quinclorac, quinmerac, quinoclamine, quizalofop-ethyl, quizalofop-P-ethyl, quizalofop-P-tefuryl, rimsulfuron, sebuthylazine, secbumeton, siduron, simazine, simetryn, S-metolachlor, SMY 1500, sodium chlorate, sulcotrione, sulfentrazone, sulfometuron-methyl, sulfosulfuron, tebuthiuron, tepraloxydim, terbacil, terbumeton, terbuthylazine, terbutryn, thenylchlor, thiazafluron, thiazopyr, thidiazimin, thifensulfuron-methyl, thiobencarb, 1-dichloroacetylazepane, tralkoxydim, tri-allat, triasulfuron, tribenuron-methyl, trichloroacetic acid, triclopyr, tridiphane, trietazine, trifloxysulfuron-sodium, trifluralin, and triflusulfuron-methyl.

Fungicides may include, but are not limited to, amino acid amide carbamates, anilinopyrimidines, antibiotics, aromatic hydrocarbons, heteroaromatics, chloro/nitrophenyls, benzamides (F), benzenesulfonamides, benzimidazoles, benzimidazole precursors, benzotriazines, carboxamides, cinnamic acids, cyanoacetamide oximes, dicarboximides, dithiolanes, DMI: imidazoles, piperazines, pyrimidines, and triazoles;

enopyranuronic acid antibiotics, heteroaromatic hydroxyanilides, MBI: dehydratases and reductases; morpholine morpholines, morpholine spiroketalamines, multi-site chloronitriles, multi-site dimethyldithiocarbamates, multi-site guanidines, multi-site inorganics, multi-site phthalimides, multi-site quinones, multi-site sulfamides, N-phenyl carbamate fungicides, organotin fungicides, phenylamide: acylalanines, phenylamide: butyrolactones, phenylamide: oxazolidinones, phenylpyrroles, phenylurea fungicides, phosphonates, phosphorothiolates, pyridazinone fungicides, pyrimidinamines, pyrimidinols, QiI, quinolines, SBI class IV: thiocarbamates, strobilurin analog: dihydrodioxazines, strobilurin type: imidazolinones, strobilurin type: methoxyacrylates, strobilurin type: ethoxycarbamates, strobilurin type: oxazolidinediones, strobilurin type: oximinoacetamides, strobilurin type: oximinoacetates, thiazolecarboxamides, thiocarbamate fungicides, and thiophenecarboxamides. Suitable fungicides include 1,2-dichloro-propane, 2-methoxyethylmercury chloride, 2-phenylphenol, 8-hydroxy-quinoline sulfate, ampropylfos, anilazine, azaconazole, azoxystrobin, benalaxyl, benodanil, benomyl, benquinox, benthiavalicarb-isopropyl, binapacryl, biphenyl, bis(tributyltin) oxide, bitertanol, blasticidin-S, borax, boscalid, bromuconazole, bupirimate, buthiobate, captafol, captan, carbendazim, carboxin, carpropamid, CGA 80 000, chinomethionat, chlobenthiazone, chloraniformethan, chloroneb, chlorothalonil, chlozolinate, climbazole, copper oxychloride, copper sulfate, copper sulfate (tribasic), cuprous oxide, cyazofamid, cyflufenamid, cymoxanil, cyproconazole, cyprodinil, cyprofuram, dazomet, dichlofluanid, dichlone, dichlorophen, diclobutrazol, diclocymet, diclomezine, dicloran, diethofencarb, difenoconazole, difenzoquat metilsulfate, diflumetorim, dimethirimol, dimethomorph, dimoxystrobin, diniconazole, dinobuton, dinocap, diphenylamine, ditalimfos, dithianon, dodemorph, dodemorph acetate, dodine, drazoxolon, edifenphos, epoxiconazole, etaconazole, etem, ethaboxam, ethirimol, etridiazole, famoxadone, fenamidone, fenarimol, fenbuconazole, fenfuram, fenhexamid, fenitropan, fenoxanil, fenpiclonil, fenpropimorph, fentin acetate, fentin hydroxide, ferimzone, fluazinam, fludioxonil, flumorph, fluoroimide, fluotrimazole, fluoxastrobin, fluquinconazole, flusilazole, flusulfamide, flutolanil, flutriafol, folpet, fosetyl-aluminum, fuberidazole, furalaxyl, furametpyr, furconazole-cis, furmecyclox, glyodin, griseofulvin, halacrinate, hexachlorobenzene, hexaconazole, hymexazol, imazalil, imibenconazole, iminoctadine triacetate, iminoctadine tris(albesilate), ipconazole, iprodione, iprovalicarb, isoprothiolane, kasugamycin hydrochloride hydrate, kresoxim-methyl, mebenil, mepanipyrim, mepronil, mercuric chloride, metalaxyl, metalaxyl-M, metconazole, methasulfocarb, methfuroxam, methyl iodide, methyl isothiocyanate, metominostrobin, metsulfovax, mildiomycin, myclobutanil, myclozolin, natamycin, nitrothal-isopropyl, nuarimol, ofurace, oleic acid, fatty acids), oxabetrinil, oxadixyl, oxpoconazole fumarate, oxycarboxin, penconazole, pencycuron, pentachlorophenol, phenylmercury acetate, phenylmercury dimethyldithiocarbamate, phenylmercury nitrate, phosphonic acid, phthalide, picoxystrobin, polyoxin B, polyoxorim, potassium bicarbonate, potassium hydroxyquinoline sulfate, prochloraz, procymidone, propamocarb hydrochloride, propiconazole, proquinazid, prothiocarb; prothiocarb hydrochloride, prothioconazole, pyracarbolid, pyraclostrobin, pyrazophos, pyributicarb, pyrimethanil, pyroquilon, quinoclamine, quinoxyfen, quintozene, silthiofam, simeconazole, sodium bicarbonate, spiroxamine, SSF-109, sulfur, tebuconazole, tecnazene, tetraconazole, thiabendazole, thicyofen, thifluzamide, thiophanate, thiophanate-methyl, thiram, tiadinil, tolclofos-methyl, tolylfluanid, triadimefon, triadimenol, triamiphos, triazoxide, trichlamide, tricyclazole, trifloxystrobin, triflumizole, triforine, triticonazole, urbacid, validamycin, vinclozolin, zarilamid, ziram, and zoxamide.

Bactericides may include, but are not limited to, bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulfate and other copper preparations.

Insecticides, acaricides and nematicides may include, but are not limited to, abamectin, ABG-9008, acephate, acequinocyl, acetamiprid, acetoprole, acrinathrin, AKD-1022, AKD-3059, AKD-3088, alanycarb, aldicarb, aldoxycarb, allethrin, alpha-cypermethrin (alphamethrin), amidoflumet, aminocarb, amitraz, avermectin, AZ-60541, azadirachtin, azamethiphos, azinphos-methyl, azinphos-ethyl, azocyclotin, *Bacillus firmus, Bacillus popilliae, Bacillus sphaericus, Bacillus subtilis, Bacillus thuringiensis, Bacillus thuringiensis* strain EG-2348, *Bacillus thuringiensis* strain GC-91, *Bacillus thuringiensis* strain NCTC-11821, *Bacillus thuringiensis israelensis*, baculoviruses, *Beauveria bassiana, Beauveria tenella*, benclothiaz, bendiocarb, benfuracarb, bensultap, benzoximate, beta-cyfluthrin, beta-cypermethrin, bifenazate, bifenthrin, binapacryl, bioallethrin, bioallethrin-5-cyclopentyl isomer, bioethanomethrin, biopermethrin, bioresmethrin, bistrifluoron, BPMC, brofenprox, bromophos-ethyl, bromopropylate, bromfenvinfos (-methyl), BTG-504, BTG-505, bufencarb, buprofezin, butathiofos, butocarboxim, butoxycarboxim, butylpyridaben, cadusafos, camphechlor, carbaryl, carbofuran, carbophenothion, carbosulfan, cartap, CGA-50439, chinomethionat, chlorantraniliprole, chlordane, chlordimeform, chloethocarb, chlorethoxyfos, chlorfenapyr, chlorfenvinphos, chlorfluazuron, chlormephos, chlorobenzilate, chloropicrin, chlorproxyfen, chlorpyrifos-methyl, chlorpyrifos (-ethyl), chlovaporthrin, chromafenozide, cis-cypermethrin, cisresmethrin, cis-permethrin, clocythrin, cloethocarb, clofentezine, clothianidin, clothiazoben, codlemone, coumaphos, cyanofenphos, cyanophos, cyantraniliprole, cycloprene, cycloprothrin, cyfluthrin, cyflumetofen, cyhalothrin, cyhexatin, cypermethrin, cyphenothrin (1R-trans-isomer), cyromazine, DDT, deltamethrin, demeton-5-methyl, demeton-5-methylsulfone, diafenthiuron, dialifos, diazinon, dichlofenthion, dichlorvos, dicofol, dicrotophos, dicyclanil, diflubenzuron, dimefluthrin, dimethoate, dimethylvinphos, dinobuton, dinocap, dinotefuran, diofenolan, disulfoton, docusat-sodium, dofenapyn, DOWCO-439, eflusilanate, emamectin, emamectin-benzoate, empenthrin (1R-isomer), endosulfan, *Entomopthora* spp., EPN, esfenvalerate, ethiofencarb, ethion, ethiprole, ethoprophos, etofenprox, etoxazole, etrimfos, famphur, fenamiphos, fenazaquin, fenbutatin oxide, fenfluthrin, fenitrothion, fenobucarb, fenothiocarb, fenoxacrim, fenoxycarb, fenpropathrin, fenpyrad, fenpyrithrin, fenpyroximate, fensulfothion, fenthion, fentrifanil, fenvalerate, fipronil, flonicamid, fluacrypyrim, fluazuron, flubendiamide, flubenzimine, flubrocythrinate, flucycloxuron, flucythrinate, flufenerim, flufenoxuron, flufenprox, flumethrin, flupyrazofos, flutenzin (flufenzine), fluvalinate, fonofos, formetanate, formothion, fosmethilan, fosthiazate, fubfenprox (fluproxyfen), furathiocarb, gamma-cyhalothrin, gamma-HCH, gossyplure, grandlure, granulosis viruses, halfenprox, halofenozide, HCH, HCN-801, heptenophos, hexaflumuron, hexythiazox, hydramethylnone, hydroprene, IKA-2002, imidacloprid, imiprothrin, indoxacarb, iodofenphos, iprobenfos, isazofos, isofenphos, isoprocarb, isoxathion, ivermectin, japonilure, kadethrin, nuclear polyhedrosis viruses, kinoprene, lambda-cyhalothrin, lindane, lufenuron, malathion, mecarbam, mesulfenfos, metaldehyde, metam-sodium, methacrifos, methamidophos, *Metharhizium anisopliae, Metharhizium flavoviride*, methidathion, methiocarb, methomyl, methoprene, methoxychlor, methoxyfenozide, metofluthrin, metolcarb, metoxadiazone, mevinphos, milbemectin, milbemycin, MKI-245, MON-45700, monocrotophos, moxidectin, MTI-800, naled, NC-104, NC-170, NC-184, NC-194, NC-196, niclosamide, nicotine, nitenpyram, nithiazine, NNI-0001, NNI-0101, NNI-0250, NNI-9768, novaluron, noviflumuron, OK-5101, OK-5201, OK-9601, OK-9602, OK-9701, OK-9802, omethoate, oxamyl, oxydemeton-methyl, *Paecilomyces fumosoroseus*, parathion-methyl, parathion (-ethyl), permethrin (cis-, trans-), petroleum, PH-6045, phenothrin (1R-trans isomer), phenthoate, phorate, phosalone, phosmet, phosphamidon, phosphocarb, phoxim, piperonyl butoxide, pirimicarb, pirimiphos-methyl, pirimiphos-ethyl, potassium oleate, prallethrin, profenofos, profluthrin, promecarb, propaphos, propargite, propetamphos, propoxur, prothiofos, prothoate, protrifenbute, pymetrozine, pyraclofos, pyrafluprole, pyresmethrin, pyrethrum, pyridaben, pyridalyl, pyridaphenthion, pyridathion, pyrimidifen, pyriprole, pyriproxyfen, quinalphos, resmethrin, RH-5849, ribavirin, RU-12457, RU-15525, rynaxapyr, S-421, S-1833, salithion, sebufos, SI-0009, silafluofen, spinosad, spirodiclofen, spiromesifen, sulfluramid, sulfotep, sulprofos, SZI-121, tau-fluvalinate, tebufenozide, tebufenpyrad, tebupirimfos, teflubenzuron, tefluthrin, temephos, temivinphos, terbam, terbufos, tetrachlorvinphos, tetradifon, tetramethrin, tetramethrin (1R-isomer), tetrasul, theta-cypermethrin, thiacloprid, thiamethoxam, thiapronil, thiatriphos, thiocyclam hydrogenoxalate, thiodicarb, thiofanox, thiometon, thiosultap-sodium, thuringiensin, tolfenpyrad, tralocythrin, tralomethrin, transfluthrin, triarathene, triazamate, triazophos, triazuron, trichlophenidine, trichlorfon, triflumuron, trimethacarb, vamidothion, vaniliprole, verbutin, *Verticillium lecanii*, WL-108477, WL-40027, yl-5201, yl-5301, yl-5302, XMC, xylylcarb, ZA-3274, zeta-cypermethrin, zolaprofos, ZXI-8901, the compound 3-methylphenyl propylcarbamate (Tsumacide Z), the compound 3-(5-chloro-3-pyridinyl)-8-(2,2,2-trifluoroethyl)-8-azabicyclo[3-.2.1]octane-3-carbonitrile (CAS-Reg. No. 185982-80-3) and the corresponding 3-endo-isomer (CAS-Reg. No. 185984-60-5) (cf. WO-96/37494, WO-98/25923), and also preparations which comprise insecticidally active plant extracts, nematodes, fungi or viruses.

As used herein, all numerical values relating to amounts, weight percentages and the like are defined as "about" or "approximately" each particular value, namely, plus or minus 10% (±10%). For example, the phrase "at least 5% by weight" is to be understood as "at least 4.5% to 5.5% by weight." Therefore, amounts within 10% of the claimed values are encompassed by the scope of the claims.

As used herein, "% wt/wt" refers to the percent weight of the material in relation to the percent weight of the formulation.

The following examples are intended to illustrate the present invention and to teach one of ordinary skill in the art how to make the formulations of the invention. They are not intended to be limiting in any way.

EXAMPLES

The following products were the sources of the materials used in the examples.

Agrimer™ VA-6 (available from Ashland) was used as the source of the binder and is a mixture of an acetic acid ethenyl ester polymer and 1-ethenyl-2-pyrrolidinone.

Tween™ 20 (available from Croda) was used as the source of the surfactant and is polyoxyethylene (20) sorbitan monolaurate.

Polyethylene glycol 200 was used as the solvent and is available from Oxiteno, BASF, and Dow.

Applicant used $GA_3$ in the form of Technical Grade Active Ingredient ("TGAI") when preparing formulations of the present invention. The percent $GA_3$ was about 96.6% w/w. Variations in the amount of $GA_3$ in the TGAI can be accounted for by decreasing or increasing the amount of solvent in order to produce the desired percent of $GA_3$ in the formulation. This is standard practice within the guidelines of U.S. Environmental Protection Agency per 40 C.F.R. § 158.175(b)(2).

Example 1

Preparation of Formulations

A concentrated $GA_3$ formulation was prepared using the amounts indicated below in Table 1 and using the following process. The solvent was warmed in a 3000 milliliter glass beaker with a stir/hot plate. Then the $GA_3$ TGAI and surfactant were added and mixed until solubilized. The binder was added and stirred until solubilized. Next, the dye was added and stirred until the formulation was homogenous. The formulation was allowed to cool and then packaged.

FD&C Red #40 was used as the source of the dye in this formulation.

TABLE 1

| Material | % wt/wt | g/batch | Purpose |
|---|---|---|---|
| $GA_3$ TGAI (96.6% pure) | 10.6 | 161 | Active Ingredient |
| PEG 200 | 84.5 | 1280 | Solvent |
| Polyoxyethylene (20) sorbitan monolaurate | 1.0 | 15 | Surfactant |
| Copolymer of acetic acid ethenyl ester polymer and 1-ethenyl-2-pyrrolidinone | 2.0 | 30 | Binder |
| Dye | 2.0 | 30 | Color additive |
| Total | 100 | 1515 | |

Accordingly, a 10.2% $GA_3$ formulation was prepared. Given the difficulty of formulating $GA_3$, it was unexpected that this concentrated formulation was homogeneous and stable.

Example 2

A concentrated $GA_3$ formulation was prepared using the amounts indicated below in Table 2 and using the following process. The solvent was warmed in a 3 liter glass beaker with a stir/hot plate. Then the $GA_3$ TGAI and surfactant were added and mixed until solubilized. The binder was added and stirred until solubilized. Next, the dye was added and stirred until the formulation was homogenous. The formulation was allowed to cool and then packaged.

FD&C Blue #1 was used as the source of the dye in this formulation.

TABLE 2

| Material | % wt/wt | g/batch | Purpose |
|---|---|---|---|
| GA$_3$ TGAI (96.6% pure) | 10.6 | 107 | Active Ingredient |
| PEG 200 | 84.5 | 853 | Solvent |
| Polyoxyethylene (20) sorbitan monolaurate | 1.0 | 10 | Surfactant |
| Copolymer of acetic acid ethenyl ester polymer and 1-ethenyl-2-pyrrolidinone | 2.0 | 20 | Binder |
| Dye | 2.0 | 20 | Color additive |
| Total | 100 | 1010 | |

Accordingly, a 10.2% GA$_3$ formulation was prepared with a batch size of 1010 grams. As indicated above in Example 1, it was unexpected that this concentrated formulation was homogeneous and stable.

The invention claimed is:

1. A concentrated agricultural liquid solution formulation consisting of:
   from about 5 to about 15% wt/wt of at least one gibberellin selected from the group consisting of gibberellic acid (GA$_3$), gibberellin$_4$ (GA$_4$), gibberellin$_7$ (GA$_7$) and gibberellin$_{4/7}$ (GA$_{4/7}$);
   from about 75 to about 90% wt/wt of polyethylene glycol 200;
   from about 0.1 to about 4% wt/wt of a binder selected from the group consisting of alkylated vinyl pyrrolidone polymers, a copolymer of acetic acid ethenyl ester and 1-ethenyl-2-pyrrolidinone, a copolymer of polyvinylpyrrolidone and 1-eicodecene and mixtures thereof;
   from about 0.1 to about 3% wt/wt of a non-ionic surfactant; and
   from about 0.1 to about 4% wt/wt of a color additive selected from the group consisting of FD&C Blue #1, FD&C Blue #2, FD&C Green #3, FD&C Red #3, FD&C Red #40, FD&C Yellow #5, FD&C Yellow #6, Citrus Red #2 and mixtures thereof.

2. The formulation of claim 1 wherein the gibberellin is GA$_3$.

3. The formulation of claim 1 wherein the at least one gibberellin is at a concentration from about 9.5 to about 11.5% wt/wt.

4. The formulation of claim 1 wherein the dye is selected from the group consisting of FD&C Blue #1 and FD&C Red #40.

5. The formulation of claim 1 wherein the binder is a copolymer of acetic acid ethenyl ester and 1-ethenyl-2-pyrrolidinone.

6. The formulation of claim 1 comprising from about 1 to about 3% wt/wt of the binder.

7. The formulation of claim 6 comprising from about 1.5 to about 2.5% wt/wt of the binder.

8. The formulation of claim 1 wherein the non-ionic surfactant is selected from the group consisting of polyoxyethylene (20) sorbitan monolaurate and polyoxyethylene (20) sorbitan monooleate.

9. The formulation of claim 8 wherein the non-ionic surfactant is polyoxyethylene (20) sorbitan monolaurate.

10. The formulation of claim 1 comprising from about 0.5 to about 1.5% wt/wt of the non-ionic surfactant.

11. A method for regulating plant growth comprising treating a plant or soil with an effective amount of the formulation of claim 1.

12. The method of claim 11 wherein the effective amount is from about 0.1 to about 50 grams of gibberellin per acre.

13. The method of claim 11 wherein the plant is rice.

14. A concentrated agricultural liquid solution formulation consisting of:
   from about 9.5 to about 11.5% wt/wt of gibberellic acid (GA$_3$);
   from about 75 to about 90% wt/wt of polyethylene glycol 200;
   from about 0.1 to about 4% wt/wt of a copolymer of acetic acid ethenyl ester polymer and 1-ethenyl-2-pyrrolidinone;
   from about 0.1 to about 3% wt/wt of polyoxyethylene (20) sorbitan monolaurate; and
   from about 0.1 to about 4% wt/wt of a color additive selected from the group consisting of FD&C Blue #1, FD&C Blue #2, FD&C Green #3, FD&C Red #3, FD&C Red #40, FD&C Yellow #5, FD&C Yellow #6, Citrus Red #2 and mixtures thereof.

15. The concentrated agricultural liquid solution formulation of claim 14 wherein:
   gibberellic acid (GA$_3$) is at a concentration of about 10.6% wt/wt;
   polyethylene glycol 200 is at a concentration of about 84.5% wt/wt;
   the copolymer of acetic acid ethenyl ester polymer and 1-ethenyl-2-pyrrolidinone is at a concentration of about 2.0% wt/wt; and
   polyoxyethylene (20) sorbitan monolaurate is at a concentration of about 1.0% wt/wt.

16. A concentrated agricultural liquid solution formulation consisting of:
   from about 5 to about 15% wt/wt of at least one gibberellin selected from the group consisting of gibberellic acid (GA$_3$), gibberellin$_4$ (GA$_4$), gibberellin$_7$ (GA$_7$) and gibberellin$_{4/7}$ (GA$_{4/7}$);
   from about 75 to about 90% wt/wt of polyethylene glycol 200;
   from about 0.1 to about 4% wt/wt of a binder selected from the group consisting of alkylated vinyl pyrrolidone polymers, a copolymer of acetic acid ethenyl ester and 1-ethenyl-2-pyrrolidinone, a copolymer of polyvinylpyrrolidone and 1-eicodecene and mixtures thereof, and
   from about 0.1 to about 3% wt/wt of a non-ionic surfactant.

17. The concentrated agricultural liquid solution formulation of claim 16 wherein:
   the at least one gibberellin is gibberellic acid (GA$_3$) at a concentration from about 9.5% to about 11.5% wt/wt;
   the binder is a copolymer of acetic acid ethenyl ester polymer and 1-ethenyl-2-pyrrolidinone; and
   the non-ionic surfactant is polyoxyethylene (20) sorbitan monolaurate.

18. The concentrated agricultural liquid solution formulation of claim 17 wherein:
   gibberellic acid (GA$_3$) is at a concentration of about 10.6% wt/wt;
   polyethylene glycol 200 is at a concentration of about 84.5% wt/wt;
   the copolymer of acetic acid ethenyl ester polymer and 1-ethenyl-2-pyrrolidinone is at a concentration of about 2.0% wt/wt; and
   polyoxyethylene (20) sorbitan monolaurate is at a concentration of about 1.0% wt/wt.

* * * * *